(12) United States Patent
Pan et al.

(10) Patent No.: US 11,238,991 B2
(45) Date of Patent: Feb. 1, 2022

(54) METHOD FOR PREDICTION OF CORTICAL SPIKING TRAINS

(71) Applicant: ZHEJIANG UNIVERSITY, Hangzhou (CN)

(72) Inventors: Gang Pan, Hangzhou (CN); Dong Xing, Hangzhou (CN); Cunle Qian, Hangzhou (CN); Yiwen Wang, Hangzhou (CN); Qiaosheng Zhang, Hangzhou (CN); Yaoyao Hao, Hangzhou (CN); Yueming Wang, Hangzhou (CN); Xiaoxiang Zheng, Hangzhou (CN); Zhaohui Wu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 294 days.

(21) Appl. No.: 16/463,686

(22) PCT Filed: Nov. 28, 2016

(86) PCT No.: PCT/CN2016/107425
§ 371 (c)(1),
(2) Date: May 23, 2019

(87) PCT Pub. No.: WO2018/094718
PCT Pub. Date: May 31, 2018

(65) Prior Publication Data
US 2019/0378622 A1 Dec. 12, 2019

(30) Foreign Application Priority Data
Nov. 24, 2016 (CN) .......................... 201611051555.4

(51) Int. Cl.
*G16H 50/50* (2018.01)
*A61B 5/00* (2006.01)
(Continued)

(52) U.S. Cl.
CPC ............... *G16H 50/50* (2018.01); *A61B 5/24* (2021.01); *A61B 5/7275* (2013.01); *G06F 2111/10* (2020.01)

(58) Field of Classification Search
CPC ........ G16H 50/50; A61B 5/24; A61B 5/7275; G06F 2111/10
See application file for complete search history.

(56) References Cited

U.S. PATENT DOCUMENTS

| | | | |
|---|---|---|---|
| 2003/0105409 A1* | 6/2003 | Donoghue | A61B 5/24 600/545 |
| 2020/0238074 A1* | 7/2020 | Song | A61N 1/36082 |
| 2020/0298005 A1* | 9/2020 | Howard | A61B 5/24 |

FOREIGN PATENT DOCUMENTS

| | | |
|---|---|---|
| CN | 102360501 | 2/2012 |
| CN | 103584855 | 2/2014 |
| WO | WO2015030606 | 3/2015 |

OTHER PUBLICATIONS

Hao, Yaoyao, et al., Motor Cortical Representation & Decoding of Moneky Reach & Grasp Movement for Brain Machine Interface, China Doctoral Dissertation Full-Text Database,.
(Continued)

*Primary Examiner* — Bijan Mapar
(74) *Attorney, Agent, or Firm* — Jiwen Chen; Jacobson Holman PLLC

(57) ABSTRACT

The present invention is related to a method for prediction of cortical spiking neural signal, comprising the following steps: 1) pretreatment of spiking neural signal, 2) modeling of posterior cortical spiking neural signal generation probability, 3) model accuracy measurement, 4) model optimization with the help of numerical gradient descent and 5) prediction of posterior cortical spiking neural signal with iterative calculation. The prediction method aims to incorporate natural features of point process of spiking neural
(Continued)

signal into the target for optimization of prediction model to improve model's capability in predicting neural spike trains.

7 Claims, 2 Drawing Sheets

(51) Int. Cl.
 *A61B 5/24* (2021.01)
 *G06F 111/10* (2020.01)

(56) References Cited

OTHER PUBLICATIONS

Aug. 15, 2013, p. 39, lines 3-6; p. 47, line 4-5; p. 51-52.

* cited by examiner

METHOD FOR PREDICTION OF CORTICAL SPIKING TRAINS

This is a U.S. national stage application of PCT Application No. PCT/CN2016/107425 under 35 U.S.C. 371, filed Nov. 28, 2016 in Chinese, claiming priority of Chinese Application No. 201611051555.4, filed Nov. 24, 2016, all of which are hereby incorporated by reference.

FIELD OF THE INVENTION

The present invention is related to the spiking trains prediction filed, in particular to a method for prediction of cortical spiking trains.

BACKGROUND ARTS

Accompanied by sustainable development of technologies on micro electrode array and profound study of brain functions in the field of modern medicine, neural spiking signal can be collected and analyzed in an extremely high temporal and spatial resolution. This can facilitate scientific research personnel to explore brain signal transmission mechanism and functional link of each cerebral cortices.

The brain can be roughly divided into numerous cortical regions according to division of different functions. It is an approach to inquire into functional links between two linked cortical regions in terms of physical distribution by using cortical spiking signal from anterior cortical region to predict cortical spiking signal from posterior cortical region. Due to the working principle on which neuron takes spiking signal as the basic unit for neuron communication, cortical signal produced by single neuron can be deemed as a time series point process. Nevertheless, most of existing models have failed to incorporate point process features of cortical signal into the model for consideration. This has brought forth certain challenges to accurate prediction of spiking signal from target cortical region and judgment of functional links between two adjacent cortical regions.

SUMMARY OF THE INVENTION

In view of disadvantages to the prior arts, the present invention aims to provide a method for prediction of cortical spiking neural signal and a method for prediction of spiking neural signal that takes generalized linear model as the basis, Discrete Time Rescaling Kolmogorov-Smirnov Statistics as the optimization target and numerical gradient as optimization approach. The main problem to be solved is to incorporate natural features for point process of spiking neural signal into the optimization target for predicted model so as to improve model's capability in predicting neural spiking trains.

The technical solution provided by the present invention to solve aforesaid problems is stated as follows:

A method for prediction of cortical spiking neural signal, characterized in that it comprises the following steps:

1) Pretreatment of cortical spiking neural signal channel: firstly, using time slot to divide original cortical spiking neural signal to complete discretization; screening out signal channels with extremely high or low spiking release rate among all cortical spiking neural signal channels;

2) Modeling of posterior cortical spiking neural signal generation probability: using mutual information to obtain numerous anterior cortical signal channels with the maximum value of mutual information with each signal channel in posterior cortical region as the independent variable of the model; after that, setting sliding window in view of each time slot in all posterior cortical signal channels to be predicted to select input independent variable of the model; once the input independent variable of the model is obtained, proceeding with modeling of posterior cortical spiking neural signal generation probability with the help of inhomogeneous Poisson point process generalized linear model;

3) Model accuracy measurement: using the model in Step 2) to obtain the sequence for spiking release probability of spiking neural signal to be predicted in the posterior cortical region; taking Discrete Time Rescaling Kolmogorov-Smirnov Statistics as the dimension for measurement of model effect to calculate model effect value;

4) Model optimization with the help of numerical gradient descent: taking the model effect measurement value obtained in Step 3) as the target function for derivation to obtain the numerical gradient; proceeding with optimized calculation of optimal parameters with Quasi-Newton Method;

5) Iterative calculation: executing Step 3) and 4) iteratively when calculating the optimal parameters until accuracy of the model corresponding to the optimized parameters is up to the local optima or upper limit of iterations; introducing final parameters into the model, and use this model to complete prediction of posterior cortical spiking neural signal.

Discretization in the Step 1) is stated as follows: Take 10 ms as the time slot width to divide original cortical spiking neural signal; record the time slot with existence of spiking neural signal in the time slot as 1 or 0 on the contrary to complete discretization.

The screening method in the Step 1) is stated as follows: First, dividing each spiking neural signal channel into 50% training set, 20% validation set and 30% test set respectively as per time axis; checking if spiking rate in three sets of the signal channel is between 2 Hz and 40 Hz; it will be deemed to be qualified through screening if this condition can be satisfied.

The method for obtainment independent variable of the model in the Step 2) is stated as follows: Once mutual information value for all pairs of spiking neural signals of anterior and posterior cortical regions is calculated, selecting the first 8 anterior cortical signal channels with the highest mutual information value with each spiking neural signal in posterior cortical region as the independent variable of model for the posterior cortical signal channel; mutual information value is stated as follows:

$$I(x_i, y_j) = \sum_{x_t \in x_i} \sum_{y_t \in y_j} p(x_t, y_t) \log\left(\frac{p(x_t, y_t)}{p(x_t)p(y_t)}\right) \quad (1)$$

wherein, $x_i$ is the signal channel i of anterior cortical region; $y_j$ is the signal channel j of posterior cortical region; $p(x_t, y_t)$ is the joint probability for simultaneous occurrence of event $x_t$ and $y_t$; $p(x_t)$ or $p(y_t)$ refers to occurrence probability of event $x_t$ or $y_t$ respectively; as original cortical spiking neural signal has been discretized, value range of $x_t$ and $y_t$ is $\{0, 1\}$.

The method for selection of input independent variable for the model in the Step 2) is stated as follows: In view of each time slot in the posterior cortical signal channel to be predicted, setting a sliding window with time span of 90 ms to intercept the first 8 anterior cortical spiking signal channels with the highest mutual information value with it as the input independent variable for the model; the end of this sliding window is in flush with current time slot.

In the Step 2), inhomogeneous Poisson point process generalized linear model is used for modeling of generation probability of posterior cortical spiking neural signal; the specific form is stated as follows:

$$P(n(t)) = \frac{e^{-\lambda(t|x(t))\Delta} * (\lambda(t|x(t))\Delta)^{n(t)}}{n(t)!} \quad (2)$$

wherein, $n(t)$ refers to the number of spikes released in time slot t; in view of discretization to original cortical spiking neural signal, value range of $n(t)$ is $\{0,1\}$; $P(n(t))$ refers to the probability for release of $n(t)$ spikes in time slot t; $\lambda(t|x(t))$ refers to density function for conditional probability for release of spikes in time slot t; $x(t)$ refers to anterior cortical spiking neural signal collected by the sliding window; $\Delta$ refers to the length of time slot;

After that, linking up $\lambda(t)$ and independent variable $x(t)$, and using exponential function as the link function of generalized linear model; specific form is stated as follows:

$$\lambda(t)\Delta = e^{x(t)^T \theta} \quad (3)$$

wherein $\lambda(t) = \lambda(t|x(t))$.

In the Step 3), Discrete Time Rescaling Kolmogorov-Smirnov Statistics are taken as the dimension for measurement of model effect to calculate model effect value; its specific form is stated as follows:

I. First, generating a new sequence $q(t)$ on the basis of $\lambda(t)$ to eliminate impact from sampling of discretization time; its specific form is stated as follows:

$$\lambda(t) = -\log(1 - \lambda(t)\Delta) \quad (4)$$

II. After that, cutting the sequence $q(t)$ in reference to the spiking trains produced by the neural cell to be predicted; once completed, integrating value $q(t)$ between two adjacent spiking signals, and correcting discrepancy incurred by discretization time treatment; the specific form is stated as follows:

$$\zeta(i) = \sum_{t=t_i+1}^{t_{i+1}} q(t) + q(t_{i+1}) \frac{\delta(i)}{\Delta} \quad (5)$$

wherein, $t_j$ refers to the occurrence time of spiking signal i of the neural cell to be predicted; $t_{i+1}$ refers to occurrence time of spiking signal $i+1$ of the neural cell to be predicted; $\delta(i)$ is a random variable collected in the following form:

$$\delta(i) = -\frac{\Delta}{q(t_{i+1})} \log(1 - r(i)(1 - e^{-q(t_{i+1})})) \quad (6)$$

$r(i)$ in Formula (6) is a random variable uniformly distributed within $[0,1]$;

III. After that, proceeding with scale transformation of $\zeta(i)$ to obtain the following formula:

$$z(i) = 1 - e^{-\zeta(i)} \quad (7)$$

According to Kolmogorov-Smirnov Test Theory, the set $\{z(i)\}$ produced by Formula (7) is to be in uniform distribution within $[0,1]$;

IV. Rearranging the set $\{z(i)\}$ in a sequence from small value to big one, and plotting it to the coordinate system for comparison while ensuring uniform distribution within standard $[0,1]$; transversing axis refers to set $\{z(i)\}$; whereas vertical axis refers to standard uniform distribution; taking the maximum value difference between the two on the vertical axis as the effect measurement value $f(y|\theta)$.

In the Step 3), calculation process for each neural cell signal channel to be predicted will be executed for 10 times for taking the mean value when calculating effect measurement value.

In the Step 4) model optimization refers to the following fact: Directly calculating numerical gradient of target function $f(y|\theta)$ through approximate derivation; the specific form for derivation of numerical gradient is stated as follows:

$$\frac{\partial f(y|\theta)}{\partial \theta_i} = \frac{f(y|\theta^a) - f(y|\theta^b)}{2\varepsilon} \quad (8)$$

wherein, y refers to spiking neural signal channel to be predicted in posterior cortical region; $\theta$ refers to the vector of model parameter to be defined; $f(y|\theta)$ refers to the target function; $\theta^a$ and $\theta^b$ are represented as $\theta_i^a = \theta_i + \epsilon$ and $\theta_i^b = \theta_i - \epsilon$ on the dimension i; value of other dimensions is consistent with $\theta$; here, value of $\epsilon$ is 1e-5.

As compared with prior arts, the present invention has the following beneficial effect: Natural features of point process of spiking neural signal is incorporated into optimization target for the prediction model to improve model's capability in prediction of neural spiking trains.

PREFERRED EMBODIMENTS

The present invention is further described as follows in combination with preferred embodiments and drawings.

Figure 1:
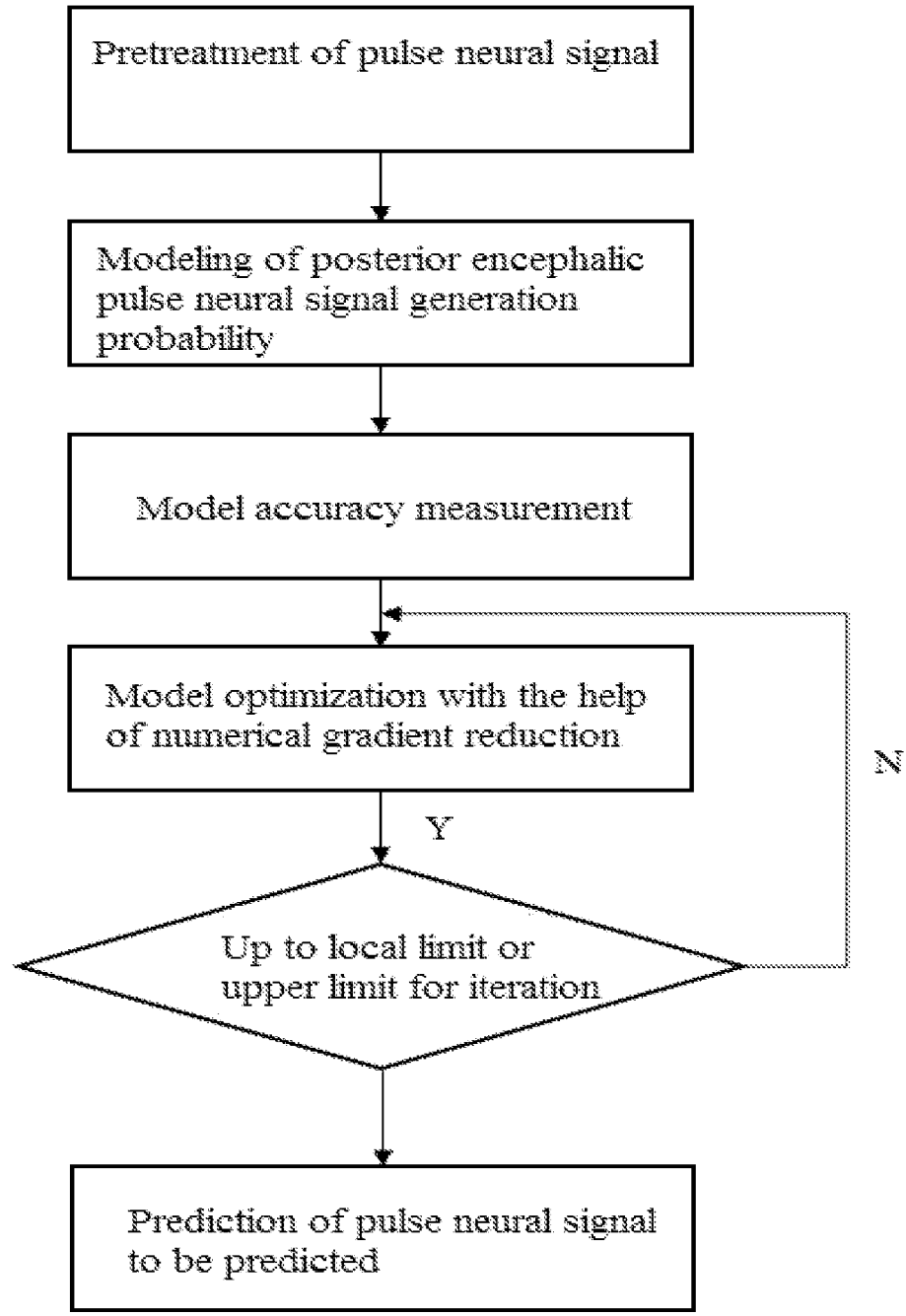
FIG. 1 is the overall flow chart for prediction of posterior cortical spiking neural signal in embodiments.
Figure 2:
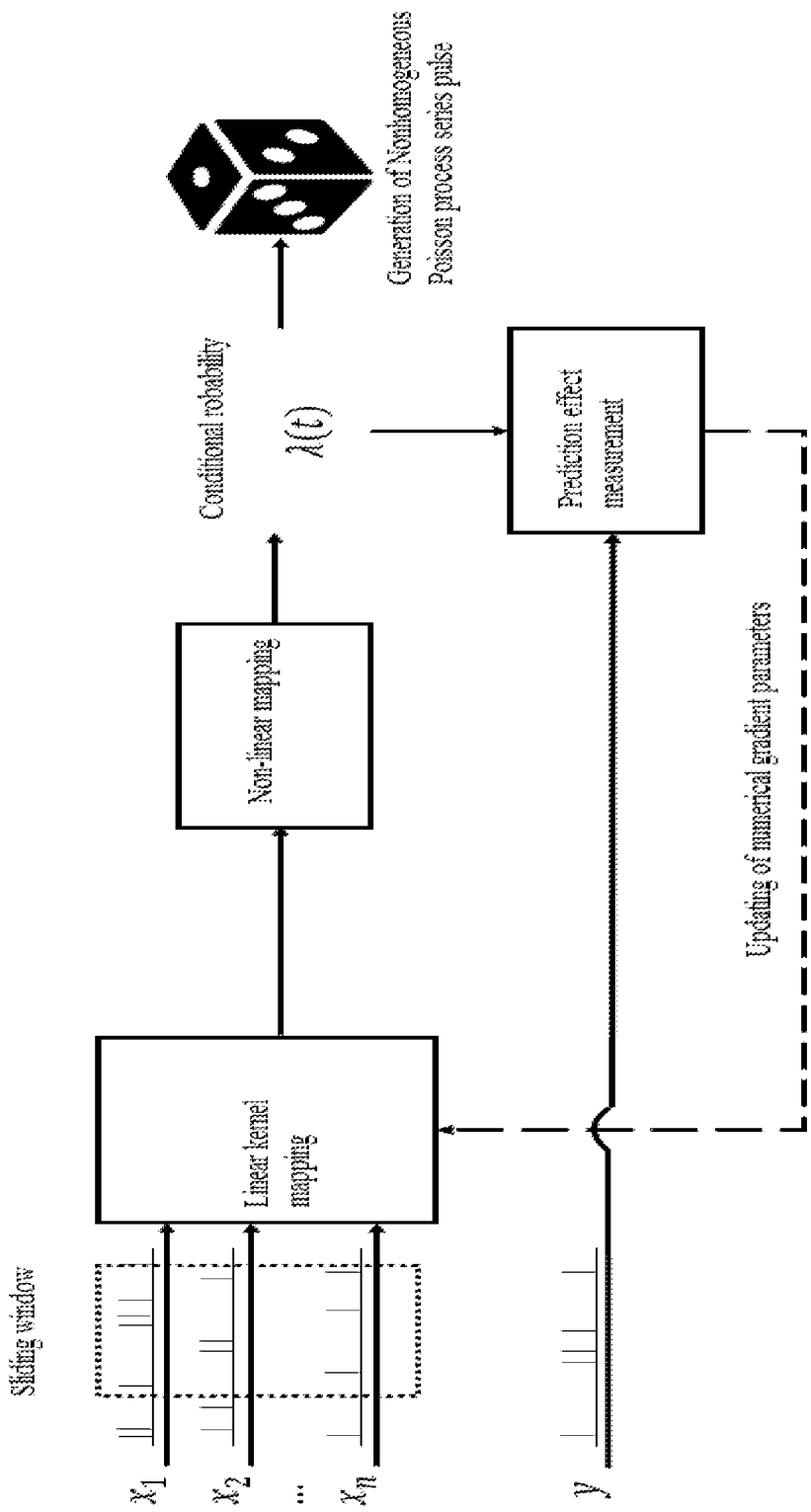
FIG. 2 is the graph showing dependence between each variable predicted by posterior spiking neural signal in embodiments.

The method for prediction of cortical spiking neural signal as shown in FIGS. 1 and 2, comprising the following steps:

(1) Pretreatment of Cortical Spiking Neural Signal Channel

First, using micro electrode array to collect original cortical spiking neural signal, and then using time slot to divide original cortical spiking neural signal to complete discretization. Specific method is stated as follows: taking 10 milliseconds as the time slot width to divide original cortical spiking neural signal; recording the time slot with existence of spiking neural signal in the time slot as 1 or 0 on the contrary to complete discretization.

After that, screening out signal channels with extremely high or low spike release rate among all cortical spiking neural signal channels; the specific method is stated as follows: First, dividing each spiking neural signal channel into 50% training set, 20% validation set and 30% test set respectively as per time axis; checking if spiking release rate in three sets of the signal channel is between 2 Hz and 40 Hz; it will be deemed to be qualified through screening if this condition can be satisfied.

(2) Modeling of Posterior Cortical Spiking Neural Signal Generation Probability

Once mutual information value for all pairs of spiking neural signals of anterior and posterior cortical regions is calculated, selecting the first 8 anterior cortical signal channels with the highest mutual information value with each spiking neural signal in posterior cortical region as the independent variable of model for the posterior cortical signal channel; mutual information value is stated as follows:

$$I(x_i, y_j) = \sum_{x_t \in x_i} \sum_{y_t \in y_j} p(x_t, y_t) \log\left(\frac{p(x_t, y_t)}{p(x_t)p(y_t)}\right) \quad (1)$$

wherein, $x_i$ is the signal channel i of anterior cortical region; $y_j$ is the signal channel j of posterior cortical region; $p(x_t, y_t)$ is the joint probability for simultaneous occurrence of event $x_t$ and $y_t$; $p(x_t)$ or $p(y_t)$ refers to occurrence probability of event $x_t$ or $y_t$ respectively; as original cortical spiking neural signal has been discretized, value range of $x_t$ and $y_t$ is $\{0, 1\}$.

In view of each time slot in the posterior cortical signal channel to be predicted, setting a sliding window with time span of 90 milliseconds to intercept the first 8 anterior cortical spiking signal channels with the highest mutual information value with it as the input independent variable for the model; the end of this sliding window is in flush with current time slot.

Once the input independent variable for the model is obtained, using inhomogeneous Poisson point process generalized linear model for modeling of generation probability of posterior cortical spiking neural signal; the specific form is stated as follows:

$$P(n(t)) = \frac{e^{-\lambda(t|x(t))\Delta} * (\lambda(t|x(t))\Delta)^{n(t)}}{n(t)!} \quad (2)$$

wherein, n(t) refers to the number of spikes released in time slot t; in view of discretization to original cortical spiking neural signal, value range of n(t) is $\{0,1\}$; P (n(t)) refers to the probability for release of n(t) spikes in time slot t; $\lambda(t|x(t))$ refers to density function(abbreviated as $\lambda(t)$) for conditional probability for release of spikes in time slot t; x(t) refers to anterior cortical spiking neural signal collected by the sliding window; $\Delta$ refers to the length of time slot;

After that, linking up $\lambda(t)$ and independent variable x(t), and use exponential function as the link function of generalized linear model; specific form is stated as follows:

$$\lambda(t)\Delta = e^{x(t)^T \theta} \quad (3)$$

wherein $\lambda(t) = \lambda(t|x(t))$, (3) Model Accuracy Measurement

Using the model in Step 2) to obtain the series for spiking release probability of spiking neural signal to be predicted in posterior cortical region; taking Discrete Time Rescaling Kolmogorov-Smirnov Statistics as the dimension for measurement of model effect to calculate model effect measurement value; the specific form is stated as follows:

I. Firstly, generating a new sequence q(t) on the basis of $\lambda(t)$ to eliminate impact from sampling of discretization time; its specific form is stated as follows:

$$q(t) = -\log(1 - \lambda(t)\Delta) \quad (4)$$

II. After that, cutting the sequence q(t) in reference to the spiking trains produced by the neural cell to be predicted; once completed, integrating value q(t) between two adjacent spiking signals, and correcting discrepancy incurred by discretization time treatment; the specific form is stated as follows:

$$\zeta(i) = \sum_{t=t_i+1}^{t_{i+1}} q(t) + q(t_{i+1})\frac{\delta(i)}{\Delta} \quad (5)$$

wherein, $t_i$ refers to the occurrence time of spiking signal i of the neural cell to be predicted; $t_{i+1}$ refers to occurrence time of spiking signal i+1 of the neural cell to be predicted; $\delta(i)$ is a random variable collected in the following form:

$$\delta(i) = -\frac{\Delta}{q(t_{i+1})}\log(1 - r(i)(1 - e^{-q(t_{i+1})})) \quad (6)$$

r(i) in Formula (6) is a random variable uniformly distributed within [0,1];

III. After that, proceeding with scale transformation of $\zeta(i)$ to obtain the following formula:

$$z(i) = 1 - e^{-\zeta(i)} \quad (7)$$

According to Kolmogorov-Smirnov Test Theory, the set $\{z(i)\}$ produced by Formula (7) is to be in uniform distribution within [0,1];

IV. Rearranging the set $\{z(i)\}$ in a sequence from small value to big one, and plotting it to the coordinate system for comparison while ensuring uniform distribution within standard [0,1]; transversing axis refers to set $\{z(i)\}$; whereas vertical axis refers to standard uniform distribution; taking the maximum value difference between the two on the vertical axis as the effect measurement value $f(y|\theta)$. As effect measurement value $f(y|\theta)$ may change accompanied by variation to model parameter $\theta$, it can be deemed as a function of $\theta$, namely target function of the model (here, y refers to a posterior cortical spiking neural signal channel to be predicted). As random variable is introduced during calculation, calculation of effect measurement value is to be executed for numerous times so as to take the mean value to eliminate impact. For each neuron signal channel to be predicted, it is necessary to execute calculation for 10 times, and take the mean value.

(4) Model Optimization with the Help of Numerical Gradient Decent

Taking the effect measurement value $f(y|\theta)$ of model as obtained in Step 3) as the target function to further obtain the numerical gradient through derivation of target function; proceeding with optimized calculation of optimal parameters with Quasi-Newton Method;

Directly calculating numerical gradient of target function $f(y|\theta)$ through approximate derivation; the specific form for derivation of numerical gradient is stated as follows:

$$\frac{\partial f(y|\theta)}{\partial \theta_i} = \frac{f(y|\theta^a) - f(y|\theta^b)}{2\varepsilon} \quad (8)$$

wherein, y refers to spiking neural signal channel to be predicted in posterior cortical region; $\theta$ refers to the vector of model parameter to be defined; $f(y|\theta)$ refers to the target function; $\theta^a$ and $\theta^b$ are represented as $\theta_i^a = \theta_i + \epsilon$ and $\theta_i^b = \theta_i - \epsilon$ on the dimension i; value of other dimensions is consistent with θ; here, value of ϵ is 1e-5.

Once derivative value of the target function is obtained through approximate calculation based on numerical gradient, using Quasi-Newton Method for optimal calculation. As calculation of numerical gradient is time consuming, optimization with Quasi-Newton Method is available for quicker convergence to local optima as compared with steepest descend method. Therefore, it can minimize iteration and calculation frequency.

(5) Iterative Calculation

Step 3) and 4) were executed iteratively when calculating the optimal parameters until accuracy of the model corresponding to the optimized parameters is up to the local optima or upper limit of iterations. As a criteria judgment of local optima reached, target function of the model will no longer reduce accompanied by new around of iteration. The upper limit for the preset iteration frequency is 400. The parameter optimization process was directly exited without proceeding with new round of parameter iteration if upper limit for iteration frequency is reached. Final parameters were introduced into the model, and this model was used to complete prediction of posterior cortical spiking neural signal.

Effect Comparison

Test results of the present invention were verified by neuron spiking signal collected by Qiushi Academy for Advanced Studies of Zhejiang University from PMd and M1 cortical regions of macaque (No. B04). The signal was collected under the background that macaque was executing center-out task in four direction, of which valid length was up to 636.4 s. It comprised 127 PMd cortical neuron spiking signal channels and 102 M1 cortical neuron spiking signal channels. 96 valid PMd signal channels and 57 valid M1 signal channels were obtained through screening.

The experiment effect of the present invention was compared with effect of several other spiking signal models, including linear regression model (LR), Spike-Triggered Average(STA), Spike-Triggered Convaiance (STC), conventional generalized linear model (GLM) and so on. Table 1 showed parallel comparison between this method and several other methods in terms of spiking signal prediction effect; wherein, DTR-KS is abbreviation of Discrete Time Rescaling Kolmogorov Smirnov Test, of which value is within [0,1]; the value that is more approximate to zero indicates better prediction effect of the model.

TABLE 1

Effect Comparison between This Method and Several Other Prediction Methods

| Prediction method | Mean value of DTR-KS | M1 cortical signal channel with the optimal effect obtained with this method |
|---|---|---|
| Linear regression model | 0.1395 (±0.0627) | 10 |
| STA | 0.1241 (±0.0546) | 12 |
| STC | 0.1387 (±0.0865) | 2 |
| GLM | 0.1176 (±0.0481) | 6 |
| This method | 0.1134 (±0.0463) | 27 |

The invention claimed is:

1. A method for prediction of encephalic pulse neutral signal of a subject, characterized in that the method comprises the following steps in the following order:

1) collecting original encephalic pulse neural signal from the subject by using micro electrode array; dividing the original encephalic pulse neutral signal into a plurality of time slots by using 10 milliseconds as a time slot breadth; designating the time slot with existence of the original pulse neural signal in the time slot as 1 and designating the time slot without existence of the original pulse neural signal in the time slot as 0 to complete discretization; dividing each pulse neural signal channel into 50% training set, 20% verification set and 30% test set respectively along a time axis; checking whether pulse release rate in the training set, the verification set and the test set of the signal channel is between 2 Hz and 40 Hz; screening out signal channels with pulse release rate that is not between 2 Hz and 40 Hz;

2) using mutual information to obtain numerous anterior encephalic signal channels with the maximum value of mutual information with each signal channel in posterior encephalic region as an independent variable of a model of posterior encephalic pulse neutral signal generation probability; after that, setting sliding window in view of each time slot in all posterior encephalic signal channels to be predicted to select input independent variable of the model; once the input independent variable of the model is obtained, proceeding with modeling of posterior encephalic pulse neutral signal generation probability by using Nonhomogeneous Poisson point process generalized linear model;

3) using the model in Step 2) to obtain a sequence for pulse release probability of pulse neural signal to be predicted in the posterior encephalic region; using Discrete Time Rescaling Kolmogorov-Smirnov Statistics as a dimension for measurement of model effect to calculate model effect value;

4) taking the model effect measurement value obtained in Step 3) as a target function for derivation to obtain a numerical gradient; proceeding with optimized calculation of optimal parameters with Quasi-Newton Method;

5) executing Step 3) and 4) iteratively when calculating optimal parameters until accuracy of the model corresponding to the optimized parameters is up to a local limit point or upper limit of iterations; introducing final parameters into the model, and using the model to complete prediction of posterior encephalic pulse neutral signal; and 6) outputting predicted posterior encephalic pulse neutral signal through a display device.

2. The method for prediction of encephalic pulse neutral signal according to claim 1, characterized in that the method for obtainment independent variable of the model in the Step 2) is stated as follows: once two-two mutual information value for all pulse neutral signals of anterior and posterior encephalic regions is calculated, selecting first 8 anterior encephalic signal channels with the highest mutual information value with each pulse neural signal in posterior encephalic region as the independent variable of model for the posterior encephalic signal channel; mutual information value is stated as follows:

$$I(x_i, y_j) = \sum_{x_t \in x_i} \sum_{y_t \in y_j} p(x_t, y_t) \log\left(\frac{p(x_t, y_t)}{p(x_t)p(y_t)}\right) \quad (1)$$

wherein, $x_i$ is the signal channel i of anterior encephalic region; $y_j$ is the signal channel j of posterior encephalic region; $p(x_t, y_t)$ is the joint probability for simultaneous occurrence of event $x_t$ and $y_t$; $p(x_t)$ or $p(y_t)$ refers to occurrence probability of event $x_t$ or $y_t$ respectively; as original encephalic pulse neural signal has been discretized, value range of $x_t$ and $y_t$ is $\{0, 1\}$.

3. The method for prediction of encephalic pulse neutral signal according to claim 2, characterized in that the method for selection of input independent variable for the model is stated as follows: in view of each time slot in the posterior encephalic signal channel to be predicted, setting a sliding window with time span of 90 milliseconds to intercept the first 8 anterior encephalic pulse signal channels with the highest mutual information value with it as the input independent variable for the model; the end of this sliding window is in flush with current time slot.

4. The method for prediction of encephalic pulse neutral signal according to claim 3, characterized in that in the Step 2), Nonhomogeneous Poisson point process generalized linear model is used for modeling of generation probability of posterior encephalic pulse neutral signal; the specific form is stated as follows:

$$P(n(t)) = \frac{e^{-\lambda(t|x(t))\Delta} * (\lambda(t \mid x(t))\Delta)^{n(t)}}{n(t)!} \quad (2)$$

wherein, $n(t)$ refers to the number of pulses released in time slot t; in view of discretization to original encephalic pulse neutral signal, value range of $n(t)$ is $\{0,1\}$; $P(n(t))$ refers to the probability for release of $n(t)$ pulses in time slot t; $\lambda(t|x(t))$ refers to density function for conditional probability for release of pulses in time slot t; $x(t)$ refers to anterior encephalic pulse neutral signal collected by the sliding window; $\Delta$ refers to the length of time slot;

then, linking up $\lambda(t)$ and independent variable $x(t)$, and using exponential function as the universalized linear model to link function; specific form is stated as follows:

$$\lambda(t)\Delta = e^{x(t)^T \theta} \quad (3)$$

wherein $\lambda(t)=\lambda(t|x(t))$.

5. The method for prediction of encephalic pulse neutral signal according to claim 4, characterized in that in Step 3), Discrete Time Rescaling Kolmogorov-Smirnov Statistics are taken as the dimension for measurement of model effect to calculate model effect value; its specific form is stated as follows:

(I), firstly, generating a new sequence $q(t)$ on the basis of $\lambda(t)$ to eliminate impact from sampling of discretization time, which is represented by:

$$q(t)=-\log(1-\lambda(t)\Delta) \quad (4)$$

(II) then, cutting the sequence $q(t)$ in reference to the pulse sequence produced by the neural cell to be predicted; once completed, integrating value $q(t)$ between two adjacent pulse signals, and correcting discrepancy incurred by discretization time treatment, which is represented by:

$$\zeta(i) = \sum_{t=t_i+1}^{t_{i+1}} q(t) + q(t_{i+1})\frac{\delta(i)}{\Delta} \quad (5)$$

wherein, $t_i$ refers to the occurrence time of pulse signal i of the neural cell to be predicted;

$t_{i+1}$ refers to occurrence time of pulse signal i+1 of the neural cell to be predicted; $\delta(i)$ is a random variable collected in the following form:

$$\delta(i) = -\frac{\Delta}{q(t_{i+1})}\log(1 - r(i)(1 - e^{-q(t_{i+1})})) \quad (6)$$

$r(i)$ in Formula (6) is a random variable uniformly distributed within [0,1];

(III) then, proceeding with scale reduction of $\zeta(i)$ to obtain the following formula:

$$z(i)=1-e^{-\zeta(i)} \quad (7)$$

according to Kolmogorov-Smirnov Test Theory, the set $\{z(i)\}$ produced by Formula (7) is to be in uniform distribution within [0,1];

(IV) rearranging the set $\{z(i)\}$ in a sequence from small value to big one, and plotting it to the coordinate system for comparison while ensuring uniform distribution within standard [0,1]; transversing axis refers to set $\{z(i)\}$; whereas vertical axis refers to standard uniform distribution; taking the maximum value difference between the two on the vertical axis as the effect measurement value $f(y|\theta)$.

6. The method for prediction of encephalic pulse neutral signal according to claim 5, characterized in that in Step 3), calculation process for each neural cell signal channel to be predicted is executed for 10 times for taking the mean value when calculating effect measurement value.

7. The method for prediction of encephalic pulse neutral signal according to claim 5, characterized in that in Step 4) model optimization refers to the following fact: directly calculating numerical gradient of target function $f(y|\theta)$ through approximate derivation; the specific form for derivation of numerical gradient is stated as follows:

$$\frac{\partial f(y \mid \theta)}{\partial \theta_i} = \frac{f(y \mid \theta^a) - f(y \mid \theta^b)}{2\varepsilon} \quad (8)$$

wherein, y refers to pulse neural signal channel to be predicted in posterior encephalic region; $\theta$ refers to the vector of model parameter to be defined; $f(y|\theta)$ refers to the target function; $\theta^a$ and $\theta^b$ are represented as $\theta_i^a = \theta_i + \epsilon$ and $\theta_i^b = \theta_i + \epsilon$ on the dimension i; value of other dimensions is consistent with $\theta$; here, value of $\epsilon$ is 1e-5.

* * * * *